United States Patent
Sangwai (10) Patent No.: US 10,047,311 B2
(45) Date of Patent: Aug. 14, 2018

(54) SYSTEMS AND METHODS FOR GAS HYDRATE SLURRY FORMATION

(71) Applicant: INDIAN INSTITUTE OF TECHNOLOGY MADRAS, Tamil Nadu (IN)

(72) Inventor: Jitendra Sangwai, Mehekar (IN)

(73) Assignee: INDIAN INSTITUTE OF TECHNOLOGY MADRAS, Tamil Nadu (IN)

( * ) Notice: Subject to any disclaimer, the term of this patent is extended or adjusted under 35 U.S.C. 154(b) by 0 days.

(21) Appl. No.: 15/103,172

(22) PCT Filed: Dec. 11, 2014

(86) PCT No.: PCT/IB2014/066786
§ 371 (c)(1),
(2) Date: Jun. 9, 2016

(87) PCT Pub. No.: WO2015/087268
PCT Pub. Date: Jun. 18, 2015

(65) Prior Publication Data
US 2016/0376515 A1    Dec. 29, 2016

(30) Foreign Application Priority Data

Dec. 12, 2013    (IN) .......................... 5724/CHE/2013

(51) Int. Cl.
*B01F 3/02*  (2006.01)
*B01F 11/02*  (2006.01)
(Continued)

(52) U.S. Cl.
CPC .......... *C10L 3/108* (2013.01); *B01F 3/04106* (2013.01); *B01F 3/04503* (2013.01);
(Continued)

(58) Field of Classification Search
CPC ................. C10L 3/108; C10L 2290/22; C10L 2290/146; B01F 15/00396; B01F 15/06;
(Continued)

(56) References Cited

U.S. PATENT DOCUMENTS

| 3,514,274 A | 5/1970 | Cahn et al. |
| 5,964,093 A | 10/1999 | Heinemann et al. |

(Continued)

FOREIGN PATENT DOCUMENTS

| CN | 100341615 C | 10/2007 |
| CN | 101513600 A * | 8/2009 |

(Continued)

OTHER PUBLICATIONS

"Establishment of NGH Japan Co., Ltd. To be a pioneer for the commercialization of Natural Gas Hydrate Technology," Accessed at http://web.archive.org/web/20121201090618/http://www.mitsui.com/jp/en/release/2007/1189982_1364.html, Apr. 19, 2007, pp. 2.

(Continued)

*Primary Examiner* — Pamela H Weiss (57) ABSTRACT

Gas hydrate slurry formation systems are provided. The gas hydrate slurry formation system includes a cavitation chamber configured to receive a fluid and a cavitation device placed within the cavitation chamber. The cavitation device is configured to form a plurality of bubbles within the fluid in the cavitation chamber. The gas hydrate slurry formation system also includes a gas inlet configured to introduce a gas within the cavitation chamber such that the gas is entrained in the plurality of bubbles to form a plurality of gas-entrained bubbles. The plurality of gas-entrained bubbles implode within the cavitation chamber to form a gas hydrate slurry.

12 Claims, 4 Drawing Sheets

(51) Int. Cl.

| | | |
|---|---|---|
| *B01F 13/02* | (2006.01) | |
| *B01F 17/02* | (2006.01) | |
| *B01F 17/18* | (2006.01) | |
| *C10L 3/10* | (2006.01) | |
| *B01F 5/06* | (2006.01) | |
| *B01F 7/00* | (2006.01) | |
| *B01F 15/06* | (2006.01) | |
| *B01F 3/04* | (2006.01) | |
| *B01F 15/00* | (2006.01) | |
| *B01J 19/00* | (2006.01) | |
| *C07C 7/20* | (2006.01) | |

(52) U.S. Cl.
CPC ...... *B01F 3/04588* (2013.01); *B01F 3/04978* (2013.01); *B01F 5/0652* (2013.01); *B01F 7/00908* (2013.01); *B01F 11/025* (2013.01); *B01F 11/0258* (2013.01); *B01F 15/00396* (2013.01); *B01F 15/06* (2013.01); *B01F 15/065* (2013.01); *B01J 19/008* (2013.01); *C07C 7/20* (2013.01); *B01F 2003/04723* (2013.01); *B01F 2003/04971* (2013.01); *B01F 2215/0036* (2013.01); *B01F 2215/045* (2013.01); *B01F 2215/0427* (2013.01); *B01F 2215/0431* (2013.01); *B01F 2215/0454* (2013.01); *B01F 2215/0481* (2013.01); *C10L 2230/14* (2013.01); *C10L 2290/146* (2013.01); *C10L 2290/22* (2013.01)

(58) Field of Classification Search
CPC ............... B01F 3/04106; B01F 11/025; B01F 7/00908; B01F 5/0652; B01F 3/04978; B01F 3/04588; B01F 3/04503; B01F 15/065; B01F 11/0258; B01F 2215/0036; B01F 3/0803; B01F 3/0807; B01F 2003/0842; B01F 2003/0884; B01F 3/04007; B01F 3/04099; B01F 3/04241; B01F 3/04446; B01J 19/008; C07C 7/20
USPC .................................................. 366/101–107
See application file for complete search history.

(56) References Cited

U.S. PATENT DOCUMENTS

| | | | |
|---|---|---|---|
| 6,028,234 A | 2/2000 | Heinemann et al. | |
| 7,597,148 B2 | 10/2009 | O' Malley et al. | |
| 8,153,075 B2 * | 4/2012 | Nagamori ............... | C10L 3/10 422/201 |
| 8,309,031 B2 | 11/2012 | Katoh et al. | |
| 8,354,565 B1 | 1/2013 | Brown et al. | |
| 2005/0059846 A1 | 3/2005 | Kohda et al. | |
| 2005/0107648 A1 | 5/2005 | Kimura et al. | |
| 2006/0027504 A1 * | 2/2006 | Nakashima ......... | B01F 3/04609 210/695 |
| 2014/0348720 A1 * | 11/2014 | Kim .................... | B01J 19/0066 422/243 |

FOREIGN PATENT DOCUMENTS

| | | | |
|---|---|---|---|
| CN | 101955827 A * | 1/2011 | |
| EP | 835406 B1 | 9/2004 | |
| EP | 2165745 A1 | 3/2010 | |
| EP | 1836332 B1 | 11/2010 | |
| EP | 2158028 B1 | 11/2012 | |
| JP | 2006160833 A * | 6/2006 | |
| JP | 2006206635 A * | 8/2006 | |
| JP | 2007262185 A * | 10/2007 | |
| JP | 2010248449 A * | 11/2010 | |
| JP | 2010253336 A * | 11/2010 | |
| WO | 0130701 A1 | 5/2001 | |
| WO | 2008106765 A1 | 9/2008 | |
| WO | WO 2013042924 A1 * | 3/2013 | .......... B01J 19/0066 |

OTHER PUBLICATIONS

"Japan extracts gas from methane hydrate in world first," accessed at http://www.bbc.co.uk/news/business-21752441, last updated Mar. 12, 2013, pp. 2.

"Mitsui Shipbuilding Nears Practical Application of Natural Gas Hydrate Transport Technology," accessed at http://www.japanfs.org/en/news/archives/news_id026000.html, Posted on Jul. 16, 2005, pp. 2.

"Pictures: Unlocking Icy Methane Hydrates, a Vast Energy Store," accessed at http://web.archive.org/web/20141130201603/http://news.nationalgeographic.com/news/energy/2013/03/pictures/130328-methane-hydrates-for-energy/, accessed on May 30, 2016, p. 5.

International Search Report and Written Opinion for International Application No. PCT/IB14/66786, dated Jun. 8, 2015.

Kvaerner, A., and Mitsui, "Cooperation with Mitsui for gas technology," accessed at http://web.archive.org/web/20070111214149/http://www.ipt.ntnu.no/gudmundssonNGH/pressrelease.pdf, accessed on May 30, 2016, pp. 3.

Murayama, T., et al., "Effects of Guest Gas on Pelletizing Performance of Natural Gas Hydrate (NGH) Pellets," Proceedings of the 7th International Conference on Gas Hydrates (ICGH 2011), pp. 6 (Jul. 17-21, 2011).

Rajnauth, J., et al., "Gas transportation: The present and future," SPE International, pp. 17.

Takaoki, T., "Message from President," accessed at http://web.archive.org/web/20071202032605/http://www.nghjapan.mes.co.jp/english/company/index.html, accessed on May 30, 2016, pp. 3.

* cited by examiner

SYSTEMS AND METHODS FOR GAS HYDRATE SLURRY FORMATION

CROSS-REFERENCE TO RELATED APPLICATIONS

This Application is a U.S. National Stage filing under 35 U.S.C. § 371 of International Application No. PCT/IB2014/066786, filed on Dec. 11, 2014, which claims priority to Indian Patent Application No. 5724/CHE/2013, filed on Dec. 12, 2013.

BACKGROUND

Natural gas is in demand in several industrial applications such as petrochemicals, fertilizers and power plants. Natural gas can be stored in the form of liquefied natural gas (LNG) or compressed natural gas (CNG) and is transported primarily through pipelines. Pipeline transportation of natural gas can have a substantially large gestation period and is cost intensive. Moreover, pipeline transportation is not energy efficient for transportation and distribution of large volumes of natural gas.

Natural gas can be converted to gas hydrates slurries that can then be used for storage and transportation. However, the natural gas hydrates are stable only at high pressures and low temperatures. Hence, their use for transportation and storage is limited.

SUMMARY

The foregoing summary is illustrative only and is not intended to be in any way limiting. In addition to the illustrative aspects, embodiments, and features described above, further aspects, embodiments, and features will become apparent by reference to the drawings and the following detailed description.

Briefly, in accordance with one aspect, a gas hydrate slurry formation system is provided. The gas hydrate slurry formation system includes a cavitation chamber configured to receive a fluid and a cavitation device placed within the cavitation chamber. The cavitation device is configured to form a plurality of bubbles within the fluid in the cavitation chamber. The gas hydrate slurry formation system also includes a gas inlet configured to introduce a gas within the cavitation chamber such that the gas is entrained in the plurality of bubbles to form a plurality of gas-entrained bubbles. The plurality of gas-entrained bubbles implode within the cavitation chamber to form a gas hydrate slurry.

In accordance with another aspect, a method of forming a gas hydrate slurry is provided. The method includes introducing a fluid within a cavitation chamber and forming a plurality of bubbles within the fluid in the cavitation chamber by a cavitation device. The method also includes entraining a gas in the plurality of bubbles to form a plurality of gas-entrained bubbles and converting the plurality of gas-entrained bubbles to a gas hydrate slurry.

In accordance with another aspect, a method of forming a gas hydrate slurry is provided. The method includes introducing a fluid within a cavitation chamber and forming a plurality of bubbles within the fluid in the cavitation chamber by a cavitation device. The method also includes entraining a gas in the plurality of bubbles to form a plurality of gas-entrained bubbles and regulating a temperature of the cavitation chamber. The plurality of gas-entrained bubbles implode within the cavitation chamber to form a gas hydrate slurry.

DETAILED DESCRIPTION

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be used, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

It will also be understood that any compound, material or substance which is expressly or implicitly disclosed in the specification and/or recited in a claim as belonging to a group or structurally, compositionally and/or functionally related compounds, materials or substances, includes individual representatives of the group and all combinations thereof. While various compositions, methods, and devices are described in terms of "comprising" various components or steps (interpreted as meaning "including, but not limited to"), the compositions, methods, and devices can also "consist essentially of" or "consist of" the various components and steps, and such terminology should be interpreted as defining essentially closed-member groups.

Some embodiments are generally directed to techniques of forming gas hydrate slurries of gases such as natural gas. The technique provides a simple, safe and cost effective process of forming gas hydrate slurries using cavitation at substantially low temperatures. In some embodiments, hydrodynamic cavitation and/or acoustic cavitation is used to form in-situ bubbles of a fluid at localized high pressure even at ambient atmospheric conditions. Such bubbles entrain a gas to form gas-entrained bubbles that implode to form a gas hydrate slurry. Further, transportation of gas hydrate slurries formed using the present technique require substantially low capital investments and operating costs since the formed gas hydrate slurries do not require refrigeration in the carrier.

Figure 1:
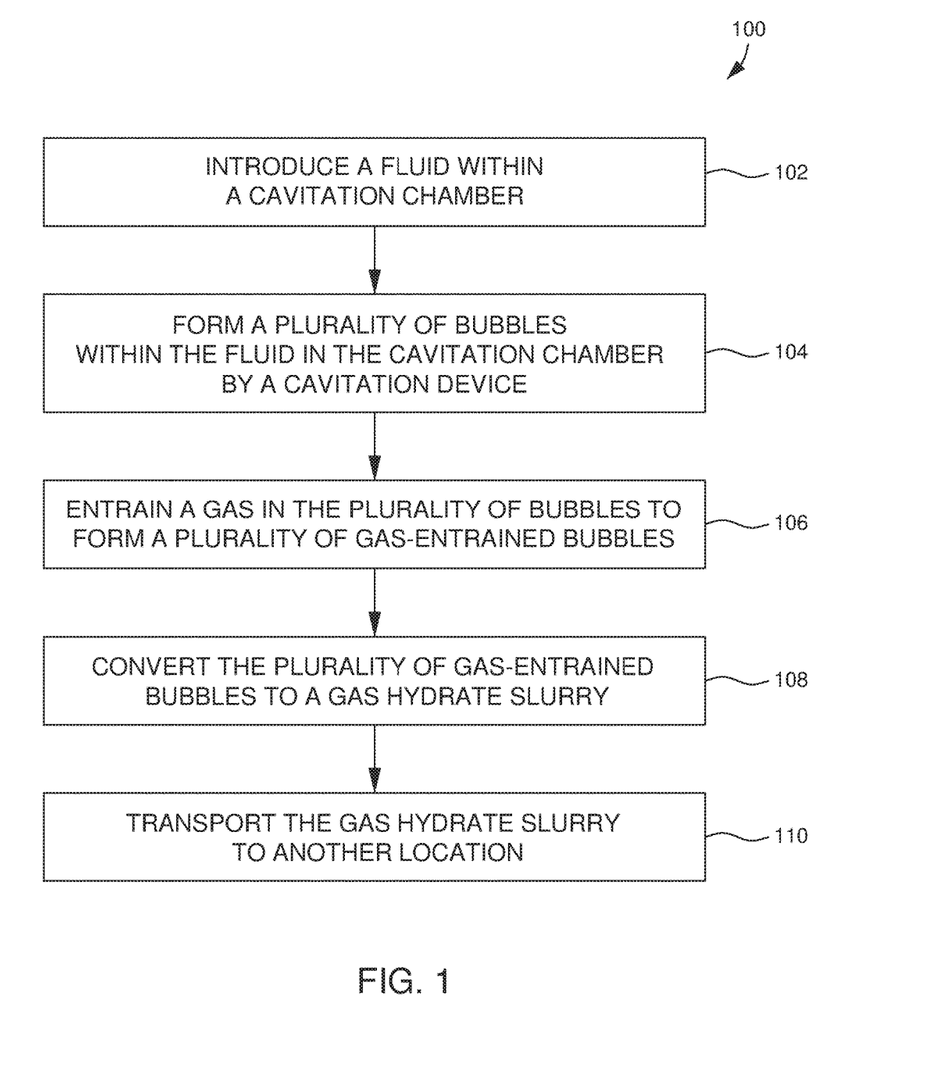
FIG. 1 is an example flow diagram of an embodiment of a method of forming a gas hydrate slurry.

Referring now to FIG. 1, an example flow diagram 100 of an embodiment for a method of forming a gas hydrate slurry is provided. At block 102, a fluid is introduced within a cavitation chamber. Examples of the cavitation chamber include, but are not limited to, a pipeline, a reactor chamber, or combinations thereof. The fluid is introduced within the cavitation chamber through a fluid inlet. In one example, the fluid includes water, other suitable fluids, or combinations of water and one or more other suitable fluids. Other suitable fluids such as alcohol, heptanes, octane ($C_8H_{18}$), decane ($C_{10}H_{22}$), dodecane ($C_{12}H_{26}$), benzene ($C_6H_6$), toluene ($C_7H_8$), petrol, gas condensate, a hydrate forming fluid, or combinations thereof may also be used.

At block 104, a plurality of bubbles are formed within the fluid in the cavitation chamber by a cavitation device. In this embodiment, the cavitation device is configured to reduce the pressure of the fluid below a vapor pressure of the fluid to facilitate formation of the plurality of bubbles. In one embodiment, the cavitation device includes a hydrodynamic cavitation device. Examples of the hydrodynamic cavitation device include a turbine, a propeller, an orifice, a venturi, an aerofoil, a channel, a micro-channel, a pipe contraction, or combinations thereof. In some other examples, the hydrodynamic cavitation device includes a rough surface, an obstruction or combinations thereof.

In another embodiment, the cavitation device includes an acoustic cavitation device. In one embodiment, the acoustic cavitation device includes one or more ultrasound transducers to facilitate formation of the bubbles within the cavitation chamber. The one or more ultrasound transducers are configured to generate ultrasound waves at a frequency of about 10 kilo Hertz (kHz) to about $10^9$ kHz. Specific example of the ultrasound wave frequency include, about 10 kHz, about $10^2$ kHz, about $10^3$ kHz, about $10^4$ kHz, about $10^5$ kHz, about $10^6$ kHz, about $10^7$ kHz, about $10^8$ kHz, about $10^9$ kHz, and ranges between any two of these values (including endpoints).

At block 106, a gas is entrained in the plurality of bubbles to form a plurality of gas-entrained bubbles. In this embodiment, the gas is introduced within the cavitation chamber through a gas inlet placed at a location downstream of the cavitation device. In one example embodiment, the gas inlet is placed at a distance downstream of the cavitation device. The downstream distance can generally be any distance. For example, the distance can be about 0.001 meters (m) to about 500 m. Specific examples of the distance of the gas inlet from the cavitation device include about 0.001 m, about 0.01 m, about 0.1 m, about 1 m, about 10 m, about 25 m, about 50 m, about 75 m, about 100 m, about 200 m, about 300 m, about 400 m, about 500 m, and ranges between any two of these values (including endpoints).

In some embodiments, the gas is introduced within the cavitation chamber through the gas inlet placed at a location upstream of the cavitation device. Examples of the gas include, but are not limited to, methane ($CH_4$), ethane ($C_2H_6$), propane ($C_3H_8$), butane ($C_4H_{10}$), pentane ($C_5H_{12}$), heptane ($C_7H_{16}$), carbon dioxide ($CO_2$), nitrogen ($N_2$), hydrogen ($H_2$), or combinations thereof.

In one example, the gas is introduced within the cavitation chamber at generally any flow rate, such as a flow rate of about 0.001 cubic meters per hour ($m^3$/hr) to about 1000 $m^3$/hr. Examples of the flow rate include, but are not limited to, 0.001 $m^3$/hr, about 1 $m^3$/hr, about 10 $m^3$/hr, about 100 $m^3$/hr, about 200 $m^3$/hr, about 300 $m^3$/hr, about 400 $m^3$/hr, about 500 $m^3$/hr, about 600 $m^3$/hr, about 700 $m^3$/hr, about 800 $m^3$/hr, about 900 $m^3$/hr, about 1000 $m^3$/hr, and ranges between any two of these values (including endpoints).

At block 108, the plurality of gas-entrained bubbles are converted to a gas hydrate slurry. In operation, the temperature of the cavitation chamber is regulated using a temperature regulation unit. The temperature can generally be any temperature. In some examples, the temperature of the cavitation chamber is maintained at about −50° C. to about 50° C. Specific examples of the temperature of the cavitation chamber include, about −50° C., about −40° C., about −30° C., about −20° C., about −10° C., about 0° C., about 10° C., about 20° C., about 30° C., about 40° C., about 50° C., and ranges between any two of these values (including endpoints).

The gas hydrate slurry is formed as the plurality of gas-entrained bubbles implode within the cavitation chamber. As the gas-entrained bubbles implode within the cavitation chamber, the gas entrained in the bubble experiences substantially high pressure. The pressure can generally be any pressure. In some embodiments, the pressure of the fluid within the plurality of gas-entrained bubbles is about 200 kilo Pascal (kPa) to about 20000 kPa as the gas-entrained bubbles implode within the cavitation chamber. Specific examples of the pressure of the fluid include, but are not limited to about 200 kPa, about 2000 kPa, about 4000 kPa, about 6000 kPa, about 8000 kPa, about 10000 kPa, about 12000 kPa, about 14000 kPa, about 16000 kPa, about 18000 kPa, about 20000 kPa, and ranges between any two of these values (including endpoints). In operation, pressure builds up within the chamber and the gas-entrained bubbles contract owing to surrounding liquid pressure eventually imploding within the chamber. Such localized high pressure along with the temperature maintained within the cavitation chamber facilitates formation of the gas hydrate slurry.

In certain embodiments, one or more thermodynamic and kinetic promoters are introduced within the cavitation chamber to facilitate formation of the gas hydrate slurry. Examples of the thermodynamic and kinetic promoters include, but are not limited to, tetra-n-butylyammonium bromide (TBAB), tetra-n-butylyammonium chloride (TBAC), tetra-n-butylyammonium fluoride (TBAF), tetrahydrofuran sodium dodecyl sulphate (SDS), or combinations thereof.

At block 110, the formed gas hydrate slurry is transported to another location. In one example embodiment, the gas hydrate slurry is transported to another location using a slurry transporter. Examples of the slurry transporter include, but are not limited to, a pipeline, a transport vehicle, or combinations thereof.

Figure 2:
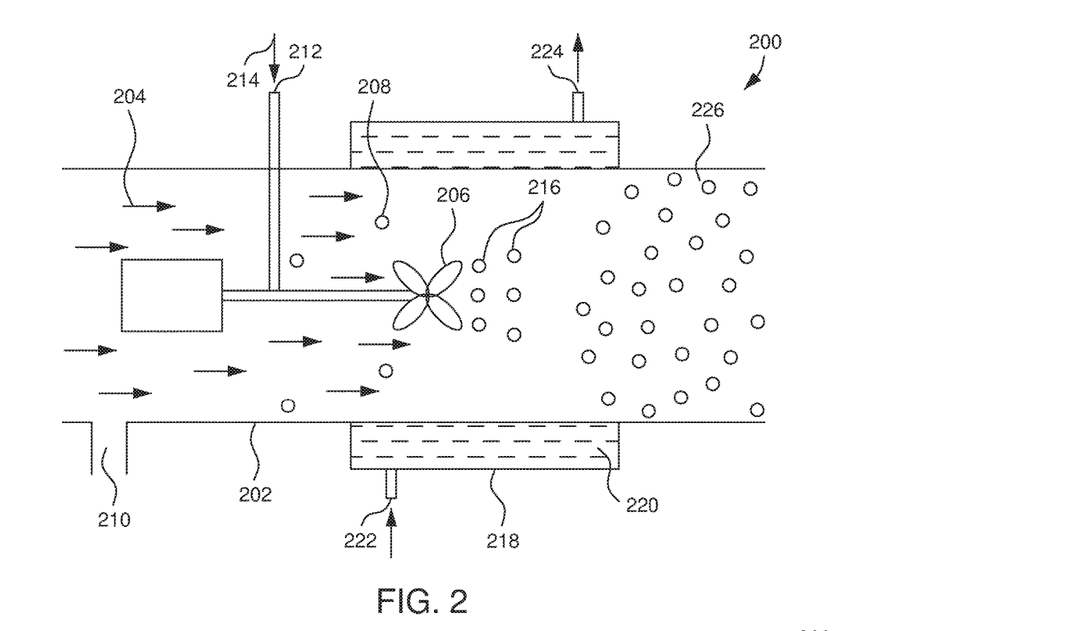
FIG. 2 is an example configuration of a gas hydrate slurry formation system using turbine as a cavitation device.

Referring now to FIG. 2, an example configuration of a gas hydrate slurry formation system 200 is illustrated. The gas hydrate slurry formation system 200 includes a cavitation chamber 202 configured to receive a fluid 204. In one example, the cavitation chamber 202 includes a pipeline. In another example, the cavitation chamber 202 includes a reactor chamber. In this embodiment, the fluid includes water. In another embodiment, the fluid includes oil. In another embodiment, the fluid can include water and oil, water and at least one other suitable fluid, oil and at least one other suitable fluid, or water, oil, and at least one other suitable fluid. Other suitable fluids such as alcohol, heptanes, octane ($C_8H_{18}$), decane ($C_{10}H_{22}$), do-decane ($C_{12}H_{26}$), benzene ($C_6H_6$), toluene ($C_7H_8$), diesel, petrol, gas condensate, a hydrate forming fluid, or combinations thereof may also be used The gas hydrate slurry formation system 200 includes at least one cavitation device 206 placed within the cavitation chamber 202. The cavitation device 206 is configured to form a plurality of bubbles 208 within the fluid 204 in the cavitation chamber 202. Examples of the cavitation device 206 include, but are not limited to, a hydrodynamic cavitation device, an acoustic cavitation device, or combinations thereof. In one example embodiment, the hydrodynamic cavitation device includes a turbine, a propeller, an orifice, a venturi, an aerofoil, a channel, a micro-channel, a pipe contraction/constriction, or combinations thereof. In this example embodiment, the cavitation device 206 includes a turbine. In this embodiment, the fluid 204 is introduced within the cavitation chamber 202 through a fluid inlet 210.

The gas hydrate slurry formation system 200 further includes at least one gas inlet 212 configured to introduce a gas 214 within the cavitation chamber 202 such that the gas is entrained in the plurality of bubbles 208 to form a plurality of gas-entrained bubbles such as represented by reference numeral 216. Examples of the gas 214 include, but are not limited to, methane ($CH_4$), ethane ($C_2H_6$), propane ($C_3H_8$), butane ($C_4H_{10}$), pentane ($C_5H_{12}$), heptane ($C_7H_{16}$), carbon dioxide ($CO_2$), nitrogen ($N_2$), hydrogen ($H_2$) or combinations thereof. In some embodiments, the gas hydrate slurry formation system 200 includes at least one gas supply (not shown) containing the gas 214.

The gas inlet 12 can be generally placed at a location upstream or downstream of the cavitation device 206. In one example, the gas inlet is placed at a distance downstream of the cavitation device 206. The distance upstream or downstream can generally be any distance. For example, the distance can be about 0.001 meters (in) to about 500 m. Specific example of the distance of the gas inlet 212 from the cavitation device 206 include, about 0.001 m, about 0.01 m, about 0.1 m, about 1 m, about 10 m, about 25 m, about 50 m, about 75 m, about 100 m, about 200 in, about 300 in, about 400 in, about 500 m, and ranges between any two of these values (including endpoints).

In one example, the gas 214 is introduced in the cavitation chamber 202 at generally any rate, such as a rate of about 0.001 cubic meters per hour ($m^3/hr$) to about 1000 $m^3/hr$. Specific example of the flow rate include, about 0.001 $m^3/hr$, about 0.01 $m^3/hr$, about 0.1 $m^3/hr$, about 1 $m^3/hr$, about 10 $m^3/hr$, about 100 $m^3/hr$, about 200 $m^3/hr$, about 3 $m^3/hr$, about 400 $m^3/hr$, about 500 $m^3/hr$, about 600 $m^3/hr$, about 700 m/hr, about 800 $m^3/hr$, about 900 $m^3/hr$, about 1000 $m^3/hr$, and ranges between any two of these values (including endpoints).

The gas hydrate slurry formation system 200 can further include at least one temperature regulation unit 218 configured to regulate a temperature of the cavitation chamber. In this example, the temperature regulation unit 218 includes a passage to circulate water 220 around the cavitation chamber 202 to maintain a suitable temperature within the cavitation chamber 202. Water 220 is introduced via an inlet 222 and is circulated through the passage 218 and is subsequently drained through an outlet 224. In this example, the water 220 is maintained at generally any desired temperature, such as a temperature of about 5° C. to about 10° C. Specific examples of the temperature include about 5° C., about 6° C., about 7° C., about 8° C., about 9° C., about 10° C., and ranges between any two of these values (including endpoints). Other suitable techniques may be used for regulating the temperature of the cavitation Chamber 202.

In some examples, the temperature of the cavitation chamber 202 is maintained at generally any desired temperature, such as a temperature of about −50° C. to about 50° C. using the temperature regulation unit 218. Specific examples of the temperature of the cavitation chamber 202 include, about −50° C., about −40° C., about −30° C., about −20° C., about −10° C., about 0° C., about 10° C., about 20° C., about 30° C., about 40° C., about 50° C., and ranges between any two of these values (including endpoints).

In operation, the turbine 206 can be rotated within the cavitation chamber 202. As the flowing stream of fluid 204 passes through the rotating turbine 206 the pressure of the fluid 204 at the tip of the turbine 206 is reduced to be relatively less than the vapor pressure of the fluid 204 thereby forming the plurality of bubbles 208. In this embodiment, the turbine 206 is rotated at generally any desired speed, such as a speed of about 50 revolutions per minute (rpm) to about $10^{10}$ rpm to form the plurality of bubbles 208 within the cavitation chamber 202. Specific examples of the rotation speed of the turbine 206 include, about 50 rpm, about 100 rpm, about $10^2$ rpm, about $10^3$ rpm, about $10^4$ rpm, about $10^5$ rpm, about $10^6$ rpm, about $10^7$ rpm, about $10^8$ rpm, about $10^9$ rpm, about $10^{10}$ rpm, and ranges between any two of these values (including endpoints).

In one example embodiment, an average size of the plurality of bubbles 208 formed in the cavitation chamber 202 is generally of any size, such as about $10^{-5}$ μm to about $10^5$ μm. Specific example of the size of the bubbles 208 include, about $10^{-5}$ μm, about $10^{-4}$ μm, about $10^{-3}$ μm, about $10^{-2}$ μm, about $10^{-1}$ μm, about 10 μm about $10^2$ μm, about $10^3$ μm, about $10^4$ μm, about $10^5$ μm, and ranges between any two of these values (including endpoints).

The plurality of bubbles 208 entrain the dissolved gas 214 to form the gas-entrained bubbles 216. Moreover, the plurality of gas-entrained bubbles 216 implode within the cavitation chamber 202 that generates a relatively high pressure condition and facilitates formation of gas hydrate slurry 226. In one example, the pressure of the fluid within the plurality of gas-entrained bubbles 216 is any desired pressure, such as about 200 kilo Pascal (kPa) to about 20000 kPa as the gas-entrained bubbles 216 implode within the cavitation chamber 202. Specific examples of the pressure of the fluid include, but are not limited to about 200 kPa, about 2000 kPa, about 4000 kPa, about 6000 kPa, about 8000 kPa, about 10000 kPa, about 12000 kPa, about 14000 kPa, about 16000 kPa, about 18000 kPa, about 20000 kPa, and ranges between any two of these values (including endpoints).

In certain embodiments, a conversion efficiency of the gas hydrate slurry formation system 200 may be estimated as a ratio of a mass of fluid that is converted into the gas hydrate slurry with respect to an initial mass of the fluid. In one example, a conversion efficiency of the gas hydrate slurry formation system 200 can be any percentage, such as about 40% to about 95%. Specific examples of the conversion efficiency include, but are not limited to, about 40%, about 50%, about 60%, about 70%, about 80%, about 95%, and ranges between any two of these values (including endpoints).

In some embodiments, the gas hydrate slurry formation system 200 includes a kinetic promoter inlet (not shown) configured to introduce one or more kinetic promoters within the cavitation chamber 202 to facilitate formation of the gas hydrate slurry 226. Examples of the thermodynamic and kinetic promoters include, but are not limited to, tetra-n-butylyammonium bromide (TBAB), tetra-n-butylammonium chloride (TBAC), tetra-n-butylyammonium fluoride (TBAF), tetrahydrofuran (THE), sodium dodecyl sulphate (SDS), or combinations thereof.

The gas hydrate slurry 226 thus formed is then transported to another location using a slurry transporter (not shown). Examples of the slurry transporter include, but are not limited to, a pipeline, a transport vehicle, or combinations thereof.

Figure 3:
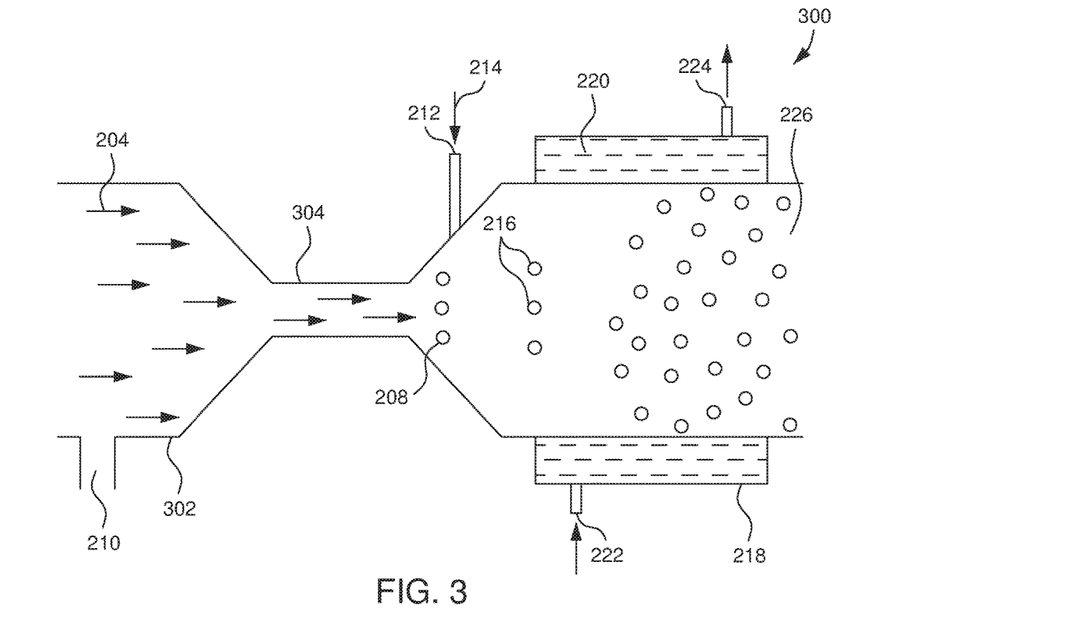
FIG. 3 is an example configuration of a gas hydrate slurry formation system using a venturi as a cavitation device.

FIG. 3 illustrates another example configuration 300 of a gas hydrate slurry formation system. In this example configuration, the gas hydrate slurry formation system 300 includes a venturi 302 as the cavitation device. As with the embodiment of FIG. 2, the venturi 302 is configured to form the plurality of bubbles 208 by hydrodynamic cavitation.

In operation, the fluid 204 is introduced within the cavitation chamber 202 through the fluid inlet 210. In one example, the fluid includes water. As the fluid 204 is introduced at a substantially high speed in the cavitation chamber 202, the plurality of bubbles 208 are formed adjacent to a throat 304 of the venturi 302. The flowing stream of fluid 204 is obstructed at the throat 304 of the venturi 302 and the pressure of fluid 204 is reduced substantially resulting in formation of the plurality of bubbles 208.

Moreover, the gas 214 is introduced within the cavitation chamber 202 through the gas inlet 212. In this embodiment, the gas 214 is introduced at a location downstream of the throat 304 of the venturi 302. Examples of the gas 214 include, but are not limited to, methane ($CH_4$), ethane ($C_2H_6$), propane ($C_3H_8$), butane ($C_4H_{10}$), pentane ($C_5H_{12}$), heptane ($C_7H_{16}$), carbon dioxide ($CO_2$), nitrogen ($N_2$), hydrogen ($H_2$), or combinations thereof.

In one example embodiment, the gas 14 is introduced within the venturi 202 at generally any desired flow rate; such as a flow rate of about 0.001 cubic meters per hour ($m^3$/hr) to about 1000 $m^3$/hr. Specific example of the flow rate include, about 0.001 $m^3$/hr, about 0.01 $m^3$/hr, about 0.1 $m^3$/hr, about 1 $m^3$/hr, about 100 $m^3$/hr, about 200 $m^3$/hr, about 300 $m^3$/hr, about 400 $m^3$/hr, about 500 $m^3$/hr, about 600 $m^3$/hr, about 700 $m^3$/hr, about 800 $m^3$/hr, about 900 $m^3$/hr, about 1000 $m^3$/hr, and ranges between any two of these values including endpoints).

The plurality of bubbles 208 entrain the gas 214 to form the gas-entrained bubbles 216. The gas-entrained bubbles 216 implode within the cavitation chamber 202 at suitable temperature resulting in the formation of the gas hydrate slurry 226. The temperature of the cavitation chamber 202 is regulated using a temperature regulation mechanism such as the temperature regulation unit 218.

Figure 4:
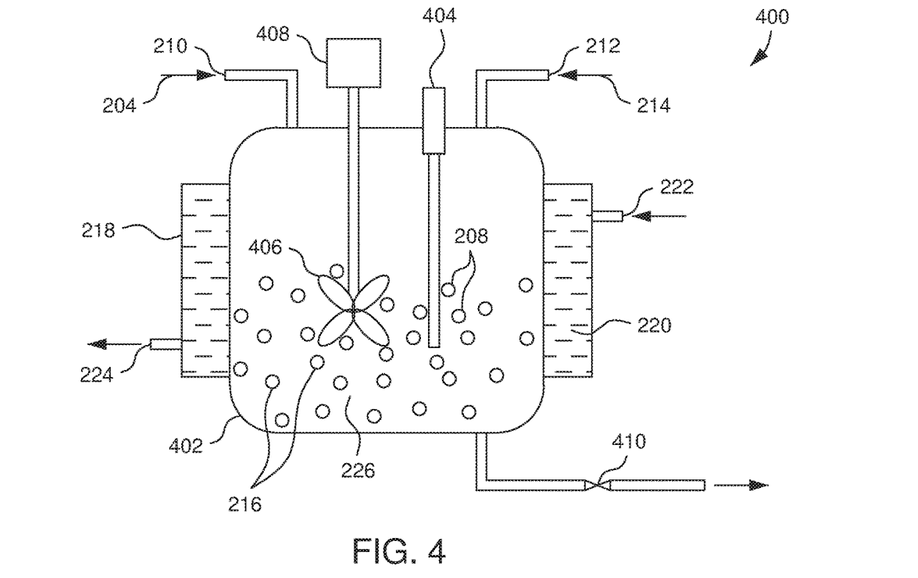
FIG. 4 is an example configuration of a gas hydrate slurry formation system using an acoustic cavitation device.

FIG. 4 illustrates an example configuration of a gas hydrate slurry formation system 400 implemented using an acoustic cavitation device. In this example configuration, the gas hydrate slurry formation system 400 includes a continuous stirred tank reactor (CSTR) 402 that functions as the cavitation chamber. As illustrated, the CSTR 402 includes the fluid inlet 210 and the gas inlet 212 to introduce the fluid 204 and the gas 214 respectively within the CSTR 402. In one example, the fluid 204 includes water. Examples of the gas 214 include, but are not limited to, methane ($CH_4$), ethane ($C_2H_6$), propane ($C_3H_8$), butane ($C_5H_{12}$), pentane ($C_5H_{12}$), heptane ($C_7H_{16}$), carbon dioxide ($CO_2$), nitrogen ($N_2$), hydrogen ($H_2$), or combinations thereof.

Further, the gas hydrate slurry formation system 400 includes at least one acoustic cavitation device 404. The acoustic cavitation device 404 includes one or more ultrasound transducers configured to generate a plurality of bubbles 208 within the CSTR 402. In some examples, the number of ultrasound transducers can generally be any number, such as about 1 to about 100. Specific examples of the number of ultrasound transducers include, about 1, about 10, about 20, about 30, about 40, about 50, about 60, about 70, about 80, about 90, about 100, and ranges between any two of these values (including endpoints).

In one example, the one or more ultrasound transducers 404 are configured to generate ultrasound waves at a frequency of about 10 kilo Hertz (kHz) to about $10^9$ kHz. Specific example of the frequency include, about 10 kHz, about $10^2$ kHz, about $10^3$ kHz, about $10^4$ kHz, about $10^5$ kHz, about $10^6$ kHz, about $10^7$ kHz, about $10^8$ kHz, about $10^9$ kHz, and ranges between any two of these values (including endpoints). The gas hydrate slurry formation system 400 also includes a stirrer 406 configured to facilitate mixing of the fluid 204 and the gas 214 to form a uniform mixture. The stirrer 406 is rotated using a motor 408. In one example, the stirrer is rotated at a speed of about 50 rpm to about $10^{10}$ rpm. Specific examples of the stirrer speed include, about 50 rpm, about $10^2$ rpm, about $10^3$ rpm, about $10^4$ rpm, about $10^5$ rpm, about $10^6$ rpm, about $10^7$ rpm, about $10^8$ rpm, about $10^9$ rpm, about $10^{10}$ rpm, and ranges between any two of these values (including endpoints)

As with the configurations 200 and 300 of FIGS. 2 and 3 respectively, the plurality of bubbles 208 entrain gas 214 to form the gas-entrained bubbles 216 within the CSTR 402. Further, the gas-entrained bubbles 216 implode at high pressure resulting in the formation of the gas hydrate slurry 226. The temperature of the CSTR 402 is regulated using a temperature regulation unit 218. The plurality of bubbles 208 formed using the ultrasound transducers 404 facilitate formation of the gas hydrate slurry 226 in substantially less time. The gas hydrate slurry thus formed is collected through an outlet 410 of the CSTR 402.

Figure 5:
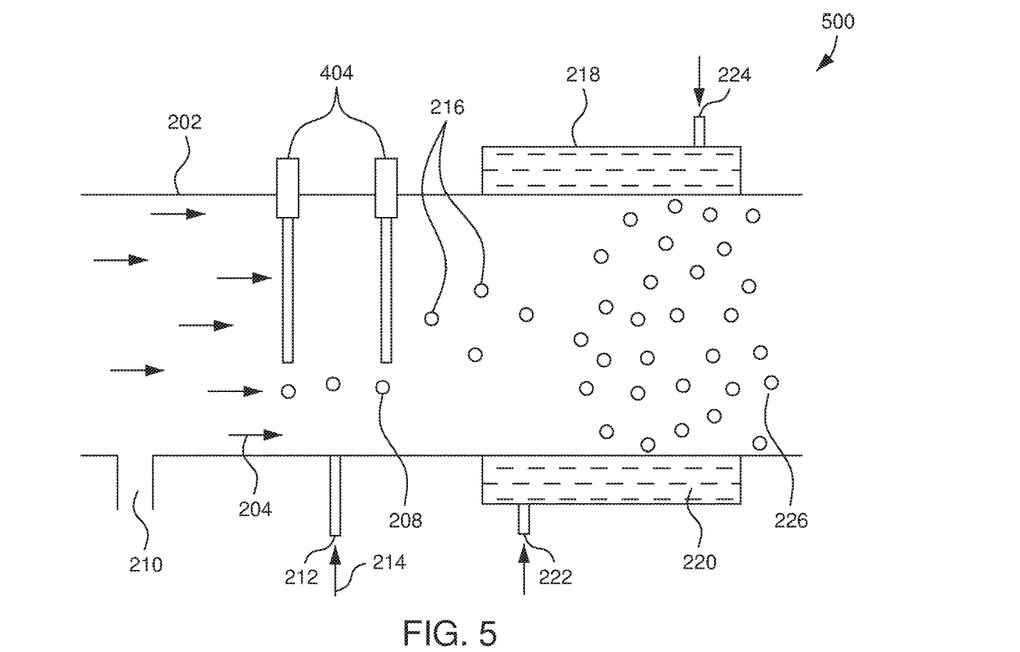
FIG. 5 is another example configuration of a gas hydrate slurry formation system.

FIG. 5 illustrates another example configuration 500 of a gas hydrate slurry formation system. The gas hydrate slurry formation system 500 includes the cavitation chamber 202. In this example configuration, the cavitation chamber is a pipeline. The fluid 204 and the gas 214 are introduced in the cavitation chamber 202 through the fluid inlet 210 and the gas inlet 12 respectively. The gas hydrate slurry formation system 500 includes one or more ultrasound transducers generally represented by reference numerals 404 to facilitate formation of bubbles 208 by acoustic cavitation within the pipeline 202. In this example, the gas hydrate slurry formation system 500 includes two ultrasound transducers.

In some examples, the number of ultrasound transducers 404 is generally any number, such as about 1 to about 100. Specific examples of the number of ultrasound transducers include, about 1, about 10, about 20, about 30, about 40, about 50, about 60, about 70, about 80, about 90, about 100, and ranges between any two of these values (including endpoints).

In one example, the one or more ultrasound transducers 404 are configured to generate ultrasound waves at a frequency of about 10 kilo Hertz (kHz) to about $10^9$ kHz. Specific example of the frequency include, about 10 kHz, about $10^2$ kHz, about $10^3$ kHz, about $10^4$ kHz, about $10^5$ kHz, about $10^6$ kHz, about $10^7$ kHz, about $10^8$ kHz, about $10^9$ kHz, and ranges between any two of these values (including endpoints).

The plurality of bubbles 208 entrain gas 214 to form the gas-entrained bubbles 216 within the pipeline 202. Further, the gas-entrained bubbles 214 implode at high pressure resulting in the formation of the gas hydrate slurry 226. The formation growth and collapse of the plurality of bubbles 208 results in substantial amount of energy with relatively higher pressure and temperatures within the pipeline 202 to drive the chemical and physical reaction in an efficient manner.

EXAMPLES

The present invention will be described below in further detail with examples and comparative examples thereof, but it is noted that the present invention is by no means intended to be limited to these examples.

Example 1: Configuration of a as Hydrate Slurry Formation System

A gas hydrate slurry formation system may be used to form gas hydrate slurry. The system can include a pipeline that may be used as the cavitation chamber and a cavitation device can be placed within the pipeline. The pipeline can be formed of a transparent acrylic sheet, commercially available from Perspex Distribution Ltd, United Kingdom. Here, the pipeline can have a diameter of about 25 cm and a length of about 5 m. The pipeline can also include a fluid inlet to introduce a fluid within the pipeline. Further, a gas inlet can be used to introduce a gas within the pipeline. A turbine can be placed at a distance of about 0.15 m downstream of the gas inlet in the pipeline to form in-situ bubbles within the fluid. The turbine can be formed of mild steel. The radius of the turbine can be about 15 cm. The turbine can be rotated within the pipeline using a motor. Further, a passage can be used to circulate water around the pipeline to regulate the temperature of the pipeline.

Example 2: Formation of a as Hydrate Slurry Using the System of Example 1

The gas hydrate slurry formation system of Example 1 may be used for forming a gas hydrate slurry. Here, a flowing stream water can be introduced within the pipeline through the fluid inlet. The turbine can be rotated within the pipeline at a speed of about 1000 rpm. As the flowing stream of water passes through the rotating turbine, the pressure of the water at the tip of the turbine can be reduced to be relatively less than the vapor pressure of the water to form bubbles within the pipeline. An average size of the plurality of bubbles formed in the pipeline can be about 100 micrometers). Moreover, methane can be introduced within the pipeline through the gas inlet at a flow rate of about 0.001 $m^3$/hr. The temperature of the pipeline can be maintained at about 5° C. by circulating water around the pipeline. The methane gas will be entrained in the bubbles to form methane-entrained bubbles. The methane-entrained bubbles can implode within the pipeline which generated a relatively high pressure condition and methane hydrate slurry can be formed.

Example 3: Conversion Efficiency of the Gas Hydrate Slurry Formation System

The conversion efficiency of the gas hydrate slurry formation system described above may be evaluated. The conversion efficiency of the gas hydrate slurry formation system can be estimated as a ratio of a mass of fluid that was converted into the gas hydrate slurry with respect to an initial mass of the fluid. The conversion efficiency of the in hydrate formation system is observed to be relatively higher than the conventional systems. In one example, a conversion efficiency of the gas hydrate slurry formation system is about 40% to about 95%. The conversion efficiency of conventional system ranges from about 40-80% and typically require high-pressure vessels for forming gas hydrate slurries. As can be seen, the present technique facilitates formation of gas hydrate slurries as the fluids flow through pipelines without the need of a high pressure vessel.

Figure 6:
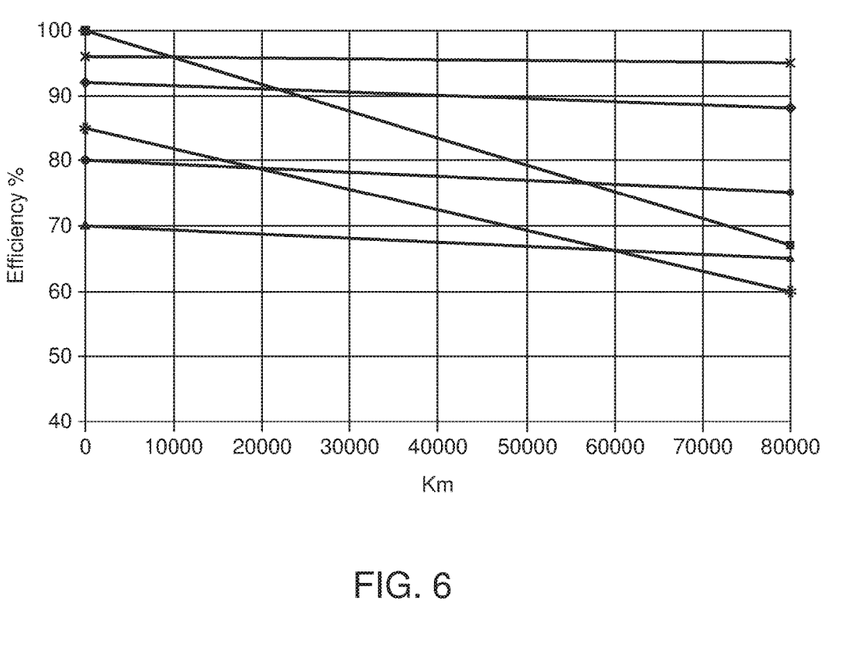
FIG. 6 is a graphical representation illustrating efficiency for different modes of natural gas transportation.

Example 4: Comparison of Transportation Efficiency of Natural Gas Transportation Modes The transportation efficiency for natural gas transportation modes was evaluated. FIG. 6 is a graphical representation of efficiency for different modes of natural gas transportation. Here, the x-axis represents distance in kilometers (km), and the y-axis represents a percent efficiency. The efficiency for natural gas transportation such as gas to liquid (triangle symbol), CNG (star symbol), methanol (round symbol), pipeline (square symbol), LNG (rhombus symbol) and gas hydrate slurry (cross symbol) is estimated over a distance of about 80000 kilometers. As can be seen, the transportation efficiency for gas hydrate slurry is about 97%, which is relatively higher as compared to other modes of transportation. Additionally, the transportation efficiency of gas hydrate slurry is independent of distance (that is, a flat horizontal line), while all other modes shown display decreasing transportation efficiency over distance (that is, a downward sloping line).

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims.

The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of claim.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present.

For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.).

It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

As will be understood by one skilled in the art, for any and all purposes, such as in terms of providing a written description, all ranges disclosed herein also encompass any and all possible sub ranges and combinations of sub ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc.

As will also be understood by one skilled in the art all language such as "up to," "at least," "greater than," "less than," and the like include the number recited and refer to ranges which can be subsequently broken down into sub ranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

I claim:

1. A method of forming a gas hydrate slurry, the method comprising:
    introducing a fluid within a cavitation chamber;
    introducing one or more thermodynamic and kinetic promoters within the cavitation chamber to facilitate formation of the gas hydrate slurry, wherein the one or more thermodynamic and kinetic promoters include at least one member selected from the group consisting of tetra-n-butylammonium bromide (TBAB), tetra-n-butylammonium chloride (TBAC), tetra-n-butylammonium fluoride (TBAF), tetrahydrofuran (THF), sodium dodecyl sulphate (SDS), and combinations thereof;
    forming a plurality of bubbles within the fluid in the cavitation chamber by a cavitation device, wherein forming the plurality of bubbles comprises forming the plurality of bubbles in-situ, by a hydrodynamic cavitation, an acoustic cavitation, or a combination thereof, wherein the hydrodynamic cavitation involves a turbine to reduce pressure of the fluid below a vapor pressure of the fluid to facilitate formation of the plurality of bubbles, wherein a rotation speed of the turbine ranges between 50 rpm to $10^{10}$ rpm;
    entraining a gas in the plurality of bubbles to form a plurality of gas-entrained bubbles; and
    converting the plurality of gas-entrained bubbles to the gas hydrate slurry.

2. The method of claim 1, wherein the fluid comprises water, alcohol, heptanes, octane ($C_8H_{18}$), decane ($C_{10}H_{22}$), do-decane ($C_{12}H_{26}$), benzene ($C_6H_6$), toluene ($C_7H_8$), diesel, petrol, a gas condensate, a hydrate forming fluid, or combinations thereof.

3. The method of claim 1, wherein the gas comprises methane ($CH_4$), ethane ($C_2H_6$), propane ($C_3H_8$), butane ($C_4H_{10}$), pentane ($C_5H_{12}$), heptane ($C_7H_{16}$), carbon dioxide ($CO_2$), nitrogen ($N_2$), hydrogen ($H_2$), or combinations thereof.

4. The method of claim 1, wherein entraining the gas in the plurality of bubbles further comprises introducing the gas at a location downstream of the cavitation device.

5. The method of claim 1, wherein forming the plurality of bubbles comprises subjecting the fluid to the pressure that is sufficient to pressurize the fluid to form the plurality of bubbles.

6. The method of claim 5, wherein the pressure of the fluid within the plurality of gas-entrained bubbles is about 2 bars to about 200 bars as the gas-entrained bubbles implode within the cavitation chamber.

7. The method of claim 1, wherein converting the plurality of gas-entrained bubbles to the gas hydrate slurry comprises maintaining the cavitation chamber at a temperature of about −50° C. to about 50° C.

8. The method of claim 7, wherein the plurality of gas-entrained bubbles implode within the cavitation chamber to form the gas hydrate slurry.

9. The method of claim 1, further comprising transporting the gas hydrate slurry from the cavitation chamber to another location using a pipeline, a transport vehicle, or a combination thereof.

10. A method of forming a gas hydrate slurry, the method comprising:
    introducing a fluid within a cavitation chamber;
    introducing one or more thermodynamic and kinetic promoters within the cavitation chamber to facilitate formation of the gas hydrate slurry, wherein the one or more thermodynamic and kinetic promoters include at least one member selected from the group consisting of tetra-n-butylammonium bromide (TBAB), tetra-n-butylammonium chloride (TBAC), tetra-n-butylammonium fluoride (TBAF), tetrahydrofuran (THF), sodium dodecyl sulphate (SDS), and combinations thereof;
    forming a plurality of bubbles within the fluid in the cavitation chamber by a cavitation device, wherein forming the plurality of bubbles comprises forming the plurality of bubbles in-situ, by a hydrodynamic cavitation, an acoustic cavitation, or a combination thereof, wherein the hydrodynamic cavitation involves a turbine to reduce pressure of the fluid below a vapor pressure of the fluid to facilitate formation of the plurality of bubbles, wherein a rotation speed of the turbine ranges between 50 rpm to $10^{10}$ rpm;
    entraining a gas in the plurality of bubbles to form a plurality of gas-entrained bubbles; and
    regulating a temperature of the cavitation chamber to form the gas hydrate slurry, wherein the plurality of gas-entrained bubbles implode within the cavitation chamber to form the gas hydrate slurry.

11. The method of claim 10, wherein the fluid comprises water, alcohol, heptanes, octane ($C_8H_{18}$), decane ($C_{10}H_{22}$), do-decane ($C_{12}H_{26}$), benzene ($C_6H_6$), toluene ($C_7H_8$), diesel, petrol, a gas condensate, a hydrate forming fluid, or combinations thereof.

12. The method of claim 10, wherein the gas comprises methane ($CH_4$), ethane ($C_2H_6$), propane ($C_3H_8$), butane ($C_4H_{10}$), pentane ($C_5H_{12}$), heptane ($C_7H_{16}$), carbon dioxide ($CO_2$), nitrogen ($N_2$), hydrogen ($H_2$), or combinations thereof.

* * * * *